(12) United States Patent
Bell et al.

(10) Patent No.: US 9,115,382 B2
(45) Date of Patent: Aug. 25, 2015

(54) KIT FOR DETECTION OF HEMOLYTIC STREPTOCOCCUS

(75) Inventors: Craig J. Bell, East Swanzey, NH (US); Leroy E. Mosher, Gilsum, NH (US)

(73) Assignees: LEROY E. MOSHER, Wake Forest, NC (US); CRAIG J. BELL, Gilsum, NH (US)

( * ) Notice: Subject to any disclaimer, the term of this patent is extended or adjusted under 35 U.S.C. 154(b) by 863 days.

(21) Appl. No.: 11/873,801

(22) Filed: Dec. 12, 2007

(65) Prior Publication Data

US 2008/0220462 A1 Sep. 11, 2008

Related U.S. Application Data

(63) Continuation-in-part of application No. 11/143,234, filed on Jun. 2, 2005, now Pat. No. 7,316,910.

(60) Provisional application No. 60/576,448, filed on Jun. 3, 2004.

(51) Int. Cl.

| C12Q 1/14 | (2006.01) |
|---|---|
| C12Q 1/04 | (2006.01) |
| G01N 33/53 | (2006.01) |
| G01N 33/542 | (2006.01) |
| C12Q 1/00 | (2006.01) |
| G01N 33/569 | (2006.01) |
| C12Q 1/60 | (2006.01) |
| C12Q 1/48 | (2006.01) |
| C12Q 1/37 | (2006.01) |
| C12Q 1/32 | (2006.01) |
| C12Q 1/28 | (2006.01) |
| A61K 38/00 | (2006.01) |

(52) U.S. Cl.
CPC . *C12Q 1/37* (2013.01); *A61K 38/00* (2013.01); *C12Q 1/04* (2013.01); *C12Q 1/14* (2013.01); *G01N 2333/315* (2013.01)

(58) Field of Classification Search
CPC ... A61K 2300/00; A61K 35/50; A61K 45/06; C12Q 1/14; C12Q 1/04
See application file for complete search history.

(56) References Cited

U.S. PATENT DOCUMENTS

| 4,544,545 | A |  | 10/1985 | Ryan et al. |
|---|---|---|---|---|
| 4,863,875 | A |  | 9/1989 | Bailey et al. |
| 5,244,806 | A | * | 9/1993 | Bang et al. ............... 435/252.33 |
| 5,374,538 | A |  | 12/1994 | Bratthall |
| 5,759,764 | A | * | 6/1998 | Polovina ........................... 435/2 |
| 5,786,137 | A | * | 7/1998 | Diamond et al. ................. 435/4 |
| 6,030,835 | A |  | 2/2000 | Musser et al. |
| 6,987,168 | B1 | * | 1/2006 | Nuttall et al. ................. 530/350 |
| 7,553,632 | B2 | * | 6/2009 | Niles et al. ...................... 435/23 |
| 2003/0125577 | A1 | * | 7/2003 | Corey et al. ................... 560/130 |
| 2005/0142622 | A1 | * | 6/2005 | Sanders et al. ............... 435/7.32 |
| 2011/0045515 | A1 | * | 2/2011 | Bell et al. ........................ 435/15 |

OTHER PUBLICATIONS

Xiao et al., Electrophoresis, 2007; 28: 233-242.*
W. Tewodros et al., Microbiology Pathology 18 (1995): 53-65.
A. Heath et al., Infectious Immunity 67 (1999): 5298-5305.
Castellino et al., "Human Plasminogen" Methods in Enzymology, vol. 80, pp. 365-378 (1981).
Unsworth, (Hylauronidase production in *Streptococcus milleri* in relation to infection, J. Clin Pathol, 1989; 42: 506-10).
Boxrud et al. "Resolution of Conformational Activation in the Kinetic Mechanism of Plasminogen Activation by *Streptokinase*" The Journal of Biological Chemistry, vol. 279, No. 35, Issue of Aug. 27, pp. 36633-36641, 2004.
McKay et al. "Plasminogen Binding by Group A *Streptococcal* Isolates from a Region of Hyperendemicity for *Streptococcal* Skin Infection and a High Incidence of Invasive Infection" Infection and Immunity, Jan. 2004, p. 364-370, vol. 72, No. 1.
Taylor et al. "Identification of Modified *Steptokinase* as the Activator of Bovine and Human Plasminogen", The Journal of Biological Chemistry, vol. 248, No. 4, Issue of Feb. 25, pp. 1127-1134, 1973.
Coleman et al. "Optimization of Enzyme-Based Assays in Coagulation Testing" Clin. Chem. 29/4, 603-608 (1983) vol. 29, No. 4.
Chibber et al. "Rapid formation of an anion-sensitive active site in stoichiometric complexes of *Streptokinase* and human [Glu1] plasminogen" Proc. Natl. Acad. Sci. USA, vol. 83, pp. 1237-1241, Mar. 1986, Biochemistry.
Rezcallah et al. "Mouse skin passage of *Streptococcus* pyogenes results in increased *Streptokinase* expression and activity" Microbiology (2004), 150, 365-371.
Tewodros et al. (*Streptokinase* activity among group A *Streptococci* in relation to *Streptokinase* genotype, plasminogen binding, and disease manifestations, Microbial Pathogenesis, 1995; 18: 53-65).

* cited by examiner

*Primary Examiner* — Gary Nickol
*Assistant Examiner* — Lakia Tongue
(74) *Attorney, Agent, or Firm* — Avery N. Goldstein, Esq.; Blue Filament Law, PLLC

(57) ABSTRACT

A reagent is provided for the detection of an exotoxin protein produced by a beta-hemolytic streptococcus bacteria suspected of being present in a host biological fluid collected from a subject. An enzyme inhibitor is present to inhibit rogue protein modification of the substrate to prevent a false positive result of the color change. A kit is provided that is readily usable by an untrained user and merely requires that an element of the kit be contacted with a biological sample and thereafter no further actions are required by the user before a discernable color change is observed with visible or UV light and a positive/negative results reference card.

21 Claims, 3 Drawing Sheets

KIT FOR DETECTION OF HEMOLYTIC STREPTOCOCCUS

CROSS REFERENCE TO RELATED APPLICATIONS

This application is a continuation-in-part of U.S. patent application Ser. No. 11/143,234 filed Jun. 2, 2005, which in turn claims priority of U.S. Provisional Patent Application Ser. No. 60/576,448 filed Jun. 3, 2004, both of which are incorporated by reference.

FIELD OF THE INVENTION

The present invention in general relates to diagnostic testing for the presence or absence of a microbe in a biological sample, and in particular to a rapid test adaptable for home use for detecting *Streptococcus pyogenes*.

BACKGROUND OF THE INVENTION

Strep throat is an infection of the pharynx caused by the bacteria *Streptococcus pyogenes*. The pharynx is that part of the throat between the tonsils and the larynx, or voice box. The main pathogenic beta-hemolytic strep groups for humans are A, C and G. More than 90% of streptococcal disease in humans may be caused by Group A beta-hemolytic strep (GABHS), although Group C is becoming increasingly recognized as an under-diagnosed condition.

*Streptococcus pyogenes* is the bacterial cause of several human infections including acute pharyngitis, impetigo, acute rheumatic fever and scarlet fever. The particular bacterium associated with these diseases are beta-hemolytic streptococci (BHS) of Groups A, C and G, of which Group A is the most dominant pathogen.

The bacteria that cause streptococcal infection such as strep throat emit toxins that result in inflammation. The initial locale of the infection is the pharyngeal mucosa. These toxins are central in facilitating the progression of the infection. Symptoms of strep throat include a sore throat that starts suddenly, without runny nose or congestion. The throat is extremely red, and swallowing is painful. White patches typically appear on the tonsils, and lymph nodes in the neck swell. Symptoms may also include fever, headache, loss of appetite and fatigue. Children with strep throat may also exhibit nausea, vomiting and abdominal distress.

Existing tests for determining when severe sore throat symptoms may be a strep infection, such as GABHS, require a visit to a physician's office or clinical laboratory. The most commonly used in-office test is an antigen-based test, specific to GABHS. These rapid strep tests require a deep swab sample of the mucus from the pharyngeal area, which is prepared using one or two reagent chemicals. The test is considered adequate for Strep A (GABHS) positive readings (sensitivity), and takes about 3-15 minutes, but negative readings (specificity) may require additional testing. When a negative rapid strep test occurs, it is common practice to perform a laboratory cell culture to confirm or rule out the presence of a Strep A infection. The culture is required owing to a high incidence of false negatives associated with the antigen specificity of current tests. Exemplary of these tests are those disclosed in U.S. Pat. Nos. 4,863,875; 5,374,538 and 6,030,835.

People who may be at risk for serious complications from strep infection include people who have chronic conditions such as diabetes, weakened immune systems or immunodeficiency disorders. Serious complications from untreated strep infection include otitis media, peritonsillar abscesses, meningitis, peritonitis, scarlet fever and rheumatic fever. Prompt diagnosis and treatment with antibiotics is the best ways to prevent infection spread and complications.

The current rapid tests require swabbing the back of the throat and tonsils to obtain a mucus sample and transferring the sample to a container or test paper. The swabbing of the throat represents a traumatic event for a patient, as well as the healthcare worker. The collection of a throat swab is made all the more difficult with pediatric patients who represent a strep-vulnerable population. With the current antigen-based tests the addition of two or more reagents is required before a visual check for the development of a color indicator. The color development is a result of GABHS antigens reacting with the antibodies introduced by the test. The methodology is sufficiently complicated to require a laboratory technician to properly perform the test, and it is too complicated for use by non-professionals.

Most sore throat symptoms, however, are due to upper respiratory viruses, and do not require immediate or extended medical care. Specifically, Group A beta-hemolytic streptococci is cultured in only approximately 15% to 20% of children with sore throats. In other words, as many as 80% of office visits are unnecessary, and "could" be avoided if a means were available for screening patients with sore throat symptoms before they seek medical care, to determine if the cause of the symptoms is associated with a virus or bacteria.

BHS Groups A, C, and G produce toxins that are known as spreading agents or invasions. One such toxin that has been well documented is streptokinase. Streptokinase is specific to these several forms of streptococcal basteria, which makes is a potential valuable biomarker for the presence of the bacteria. Streptokinase possesses no intrinsic catalytic activity but binds to plasminogen resulting in conformational expression of an active catalytic site on the zymogen without the usual strict requirement for peptide bond cleavage. Plasminogen is the zymogen of the broad-spectrum serine protease plasmin, which degrades fibrin clots and other extracellular matrix (ECM) components such as fibronectin, laminin, vitronectin, and proteoglycans. Plasminogen is activated to its enzyme state (plasmin) by the host activator tissue plasminogen activator. Plasminogen activation is a critical component in establishing invasive bacterial infections. Subversion of the host plasminogen system renders a pathogen capable of degrading ECM proteins and activating a cascade of metalloproteases, thereby conferring the potential to invade host tissue barriers. Plasmin is subsequently produced by proteolytic cleavage and the resulting streptokinase-plasmin complex propagates plasminogen activation through expression of a substrate recognition exosite.

Thus, there exists an opportunity for a non-antigen specific rapid test for the presence of clinically significant beta-hemolytic streptococcus (Groups A, C, and G) in a bodily fluid that is operative independent of a mucosal swab and additional purification or visualization enhancement steps. Additionally, there exists a need for a rapid beta-hemolytic streptococcus test that is amenable to home use as a prescreen for consultation with a health professional.

SUMMARY OF THE INVENTION

A reagent is provided for the detection of an exotoxin protein produced by a beta-hemolytic streptococcus bacteria suspected of being present in a host biological fluid collected from a subject. The substrate is modified by a BHS exotoxin protein to induce a discernable color change under visible or UV light. Further an enzyme inhibitor is present to inhibit rogue protein modification of the substrate to preventing a false positive result in the form of a color change.

A kit is provided that is readily usable by an untrained user and merely requires that an element of the kit be contacted with a biological sample and thereafter no further actions are required by the user before a discernable color change is observed with the aid of visible or UV light. The kit includes a reagent for detecting an exotoxin protein produced by a beta-hemolytic streptococcus bacterium and a reference card showing positive and negative control results and having instructions for the use thereof. The reagent contains a BHS exotoxin specific substrate and one or more enzyme inhibitor. The enzyme inhibitor suppresses rogue protein modification of the substrate to prevent a false positive result of the color change with visible or UV light.

A process is provided for detecting an exotoxin protein produced by a beta-hemolytic streptococcus bacterium suspected of being present in a biological fluid sample. The process includes mixing the biological fluid sample with one or more enzyme inhibitor to form a treated sample. By contacting the treated sample with a substrate modified preferentially by the exotoxin protein a color change is observed under visible or UV light.

BRIEF DESCRIPTION OF THE DRAWING

The current invention is described in further detail in conjunction with the following referenced drawings.

DETAILED DESCRIPTION OF THE INVENTION

Figure 1:
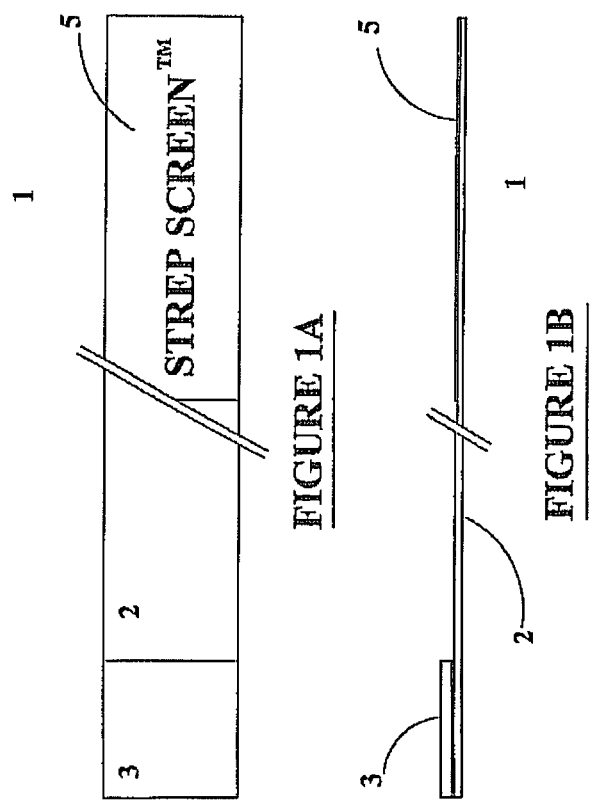
FIG. 1A is a top view and FIG. 1B is a side view of an inventive test strip.

The present invention has utility as a procedurally simple test to detect an exotoxin protein produced by beta-hemolytic streptococcus. The exotoxin protein illustratively includes streptokinase, streptolysin O, streptolysin S, hyaluronidase, streptodornase, and cysteine proteinase. The presence of the exotoxin protein in a biological sample is indicative of the presence of beta-hemolytic streptococcal bacteria (BHS) in a host. Unlike the majority of Group A BHS tests that rely on antigen-specific binding to an antibody or fragment thereof to confer specificity as to the group and strain of BHS, the present invention provides a simple indication of a generic or nonspecific BHS bacterial population being present.

As used herein "beta-hemolytic streptococcus" is defined to include those groups Streptococcus bacteria that are pathogenic through production of at least one extracellular protein, streptokinase, streptolysin, streptodornase, hyaluronidase, or cysteine proteinase. These groups specifically include A, C and G. It is appreciated that hyaluronidase and cysteine proteinase are also excreted by other organisms. Specifically, P. gingivalis produces arginine specific cysteine proteinase. Nonetheless, detection of these proteins in combination with BHS specific proteins adds to the certainty of the result.

The present invention provides a rapid detection kit for beta-hemolytic streptococcus bacteria through the reaction of an exotoxin protein produced by Group A, C, or G BHS with a substrate to induce a color change discernable by the unaided human eye. Suitable substrates may include, but are not limited to, oligopeptide p-nitroanilides or oligopeptide amido-methylcoumarins that are cleaved by the BHS exotoxin protein directly or through activation of a secondary enzyme.

Streptokinase and cysteine proteinase are representative of the exotoxin BHS proteins effective to cleave a substrate. Additionally, it is appreciated that streptolysin that is produced by BHS is an exotoxin that binds to cell membranes containing cholesterol. Streptolysin thereafter oligomerizes to form large pores in the cell membrane that effectively lyse the membrane. As a result of streptolysin action, red blood cells represent a chromogenic substrate for streptolysin. In addition, it is appreciated that a synthetic membrane containing cholesterol is readily formed that encompasses a dye species that changes appearance to the unaided eye upon the lysis of the synthetic membrane. U.S. Pat. No. 4,544,545 teaches the formation of such a lipid bilayer.

Streptokinase acts on lysine-plasminogen to convert this substrate to an active enzyme; plasmin, streptokinase-plasmin, or streptokinase-plasminogen. The active enzyme in turn reacts with an oligopeptide p-nitroanilide to free a yellow-colored aniline dye or with the oligopeptide amido-methylcoumarin to free a fluorescent dye that is visualized when excited by UV light. Substrates for plasmin, streptokinase-plasmin, or a streptokinase-plasminogen complex include commercially available substrates S-2251 (D-Val-Leu-Lys-p-Nitroanilide Dichloride), S-2403 (pyroGlu-Phe-Lys-p-Nitroanilide Hydrochloride), S-2406 (pyroGlu-Leu-Lys-p-Nitroanilide Hydrochloride), I1040 (H-D-Ala-Leu-Lys-AMC), I1390 (H-D-Val-Leu-Lys-AMC) and combinations thereof. AMC as used herein denotes fluca 1-2Galβ1-4Glc-7-amino-4-methyl-coumarin. It is appreciated that these are representative chromogenic and fluorogenic substrates for streptokinase and that other substrates such as chemiluminescent, and other fluorogenic and chromogenic oligopeptide substrates are operative in place of, or in combination with, the aforementioned oligopeptides. Streptokinase activity has previously been measured chromogenically. W. Tewodros et al., microbiology Pathology 18 (1995): 53-65.

BHS cysteine proteinase is also noted to be specific towards the chromogenic oligopeptide substrate N-succinyl Phe-Ala-p-Nitroanilide and Leu-p-Nitroanilide. It is appreciated that substrates for both streptokinase and cysteine proteinase are readily included within the inventive test kit in which greater sensitivity to the presence of BHS is desired.

An additional substrate operative for the detection of BHS is a membrane having cholesterol within the membrane and containing within the membrane volume a chromophore that changes color upon membrane lysis through oligomerization of streptolysin O or S. Membranes including cholesterol that are suitable as substrates for detection of BHS streptolysin include red blood cells and lipid bilayers including cholesterol and chromophores. The chromophores typically include hemoglobin and the aforementioned nitroanilide oligopeptides. It is appreciated that as with streptokinase substrates, cysteine proteinase and streptolysin substrates are readily provided that include a chemiluminescent, fluorogenic or other chromogenic species therein. Such chemiluminescent and fluorogenic species couplable to oligopeptides are insertable into liposomal membranes are well known to the art and are described in U.S. Pat. No. 4,544,545. Streptolysin S activity alone or in combination with streptolysin O activity has also previously been measured chromogenically. A. Heath et al., Infectious Immunity 67 (1999): 5298-5305.

Preferably, a substrate for detecting an exotoxin protein produced by beta-hemolytic streptococcus is provided within or on an inert solid matrix. Suitable materials for the formation of an inert solid matrix include cellulosic materials such as filter paper, natural fibers such as cotton, linen, silk, and wool; nitrocelluloses, carboxyalkyl celluloses, synthetic polymer fabrics such as polyamides, polylactic acids, polyacrylics and sintered polyalkylene beads. If the substrate includes a fluorescent molecule then the solid matrix should have low or no fluorescing properties.

Alternatively, solution-based substrates for BHS extracellular proteins are provided in conventional buffer solutions such as PBS (phosphate buffered saline). Preferably, a buffer solution includes an antimicrobial agent to preclude substrate degradation by opportunistic microorganisms. It is further appreciated that the shelf life of an inventive reagent and therefore a kit for performing an inventive nonspecific BHS strep test is increased by storing the reagent under cool conditions such as those found in a consumer refrigerator/freezer. In instances where substrates are in solution form, or red blood cells are provided as a substrate for streptolysin, preferably a cryopreservative is present. Typical of cryopreservative solutions are those that include 2% heta starch, 4% albumin and 7.5% dimethylsulfoxide.

Biological fluids from a host suitable for detection of BHS therein include sweat, mucosa, saliva, blood, tears, and pus. In a circumstance where one is attempting to detect BHS associated with a sore throat, the preferred biological fluid is saliva, in contrast to prior art antigenic binding that has required throat mucosa. Saliva represents a less invasive source of biological fluid for the determination as to the presence or absence of an active strep infection and is collected by buccal swab or expectoration in contrast to a throat swab. The present invention is based upon the recognition that saliva of an individual having a BHS-induced pharyngitis contains streptokinase, streptolysin, cystein proteinases and other exotoxins associated with BHS.

It should be appreciated that the various biological fluids that have been indicated as host suitable for testing for the presence or absence of BHS by detecting an exotoxin protein, such as streptokinase, also contain a vast number of other proteins. When a given substrate is found to be cleavable by rogue (non-specific and non-targeted) proteins such as trypsin, kallikrein, tissue plasminogen activator (tPA), calpain, cystatin, kinases, peroxidases, dehydrogenases, phosphorylases, transferases, reductases, mutases, and/or isomerases; other than the particular exotoxin proteins mentioned above, a proper enzyme inhibitor(s) preferentially inhibiting the rogue proteins is used. For example, trypsin is a serine protease and a digestive enzyme produced in the pancreas and found mainly in the intestines, but also at low concentrations in the stomach and in saliva. In a preferred embodiment of saliva sampling for BHS exotoxins, trypsin enzymatic activity is suppressed to enhance detection of the BHS specific exotoxin streptokinase.

Non-BHS enzyme inhibitors are provided in a biological sample or in an inventive reagent to prevent false positive testing results by minimizing or preventing the action of the rogue proteins(s) from cleaving the substrate allowing the targeted exotoxin protein to be the only one reacting with the substrate and enhancing the sensitivity of the testing results. Inhibitors illustratively include ECOTIN (Calbiochem) specifically inhibiting trypsin or Pefabloc SC (Roche) broadly inhibiting a broad spectrum of serine proteases, including trypsin. The appropriate quantity of non-BHS enzyme inhibitor is readily determined using standard solutions with known quantities of trypsin and a uniform quantity of a target BHS exotoxin.

Referring now to the figures, exemplary embodiments of the present invention are provided. Referring now to the embodiment of the invention shown in FIGS. 1A and 1B, a test strip also commonly referred to as a dipstick is shown generally at 1. The test strip 1 is preferably constructed of a thermoplastic illustratively including polystyrene and polypropylene. Thermoplastic strip 2 has an exemplary size of approximately 0.25" wide by 3" long by 0.015" thick. The test strip 1 has a solid matrix 3 which contains BHS reagent formula 4 (not shown). Solid matrix 3 is attached to plastic strip 2 by pressure-sensitive adhesive or other common laminating means, such as heat sealing. The solid matrix is the surface of the plastic dipstick or a filter material such as whatman Inc. papers CF 4 or BA 83. Test strip 1 has an area 5 that is used for labeling, as in a pressure-sensitive label or pad printing ink.

The reagent formula 4 is typically dispensed onto solid matrix 3 by a manual pipette, automated pipette, or other precision dispensing means currently known in the art. The substrates are optionally impregnated throughout the thickness of the matrix. Such saturation methods, including dip baths, enhances the extent of reaction with an active enzyme associated with BHS and illustratively includes streptokinase-plasminogen complex, streptokinase-plasmin, and plasmin. Alternate substrate application methods include various printing techniques are known for application of liquid reagents to carriers, e.g. micro-syringes, pens using metered pumps, direct printing and ink-jet printing. The volume of reagent formula 4 disposed is between 0.5 and 100 microliters. The indicating formula is then dried at room temperature or at an elevated temperature that does not denature the formula. The drying process is assisted by vacuum and/or a desiccating agent. Reagent formula 4 is reactive with a BHS extracellular protein exotoxin directly or indirectly as a result of a complex or activation of an enzyme. Preferably, the BHS protein includes at least one of streptokinase, streptolysin O, streptolysin S, and cysteine proteinase. Preferably, the reagent fluorogenically detects streptokinase. A reagent formula for streptokinase includes at least fluorogenic substrate H-D-Val-Leu-Lys-AMC (Peptides International) and optionally the single chain glycoprotein plasminogen (Sigma), which is the inactive precursor to the active enzyme plasmin and optionally at least one rogue enzyme inhibitor (Roche).

The optional addition of plasminogen to reagent formula 4 enhances the reaction between the streptokinase and endogenous plasminogen with the substrate. The plasminogen is isolated from a variety of sources. Human plasminogen is obtained from pooled plasma, gulplasminogen, lys-plasminogen, recombinant, and/or fractions of plasminogen. Lys-plasminogen is the preferred form of the zymogen for reagent formula 4 because it is 20 times more reactive than the glu-plasminogen form. Since the vast majority of plasminogen in human blood is glu-plasminogen, lys-plasminogen is manufactured from purified glu-plasminogen. By plasmin hydrolysis of the Lys76-Lys-77 peptide bond of glu-plasminogen, lys-plasminogen is formed. The process then involves a plasmin quenching process and lys-plasminogen purification process.

Biological protein stabilizers are optionally included into reagent chemistry formulation 4. Bovine serum albumin (Sigma) and Prionex (Centerchem) are protein stabilizers that improve a proteinaceous substrate shelf life.

Reaction enhancement additives are another component that can optionally be included into reagent formula 4. These additives induce a conformational change to the molecular structure of the streptokinase, the lys-plasminogen, or both to states that favor the reaction and accelerated the outcome. These additives include, but are not limited to, non-ionic detergents such as Triton (Fisher Scientific) and mammalian protein fibrin, or protein fibrinogen (Sigma) or poly peptides with a lysine binding site (poly-D-lysine).

Figure 2:
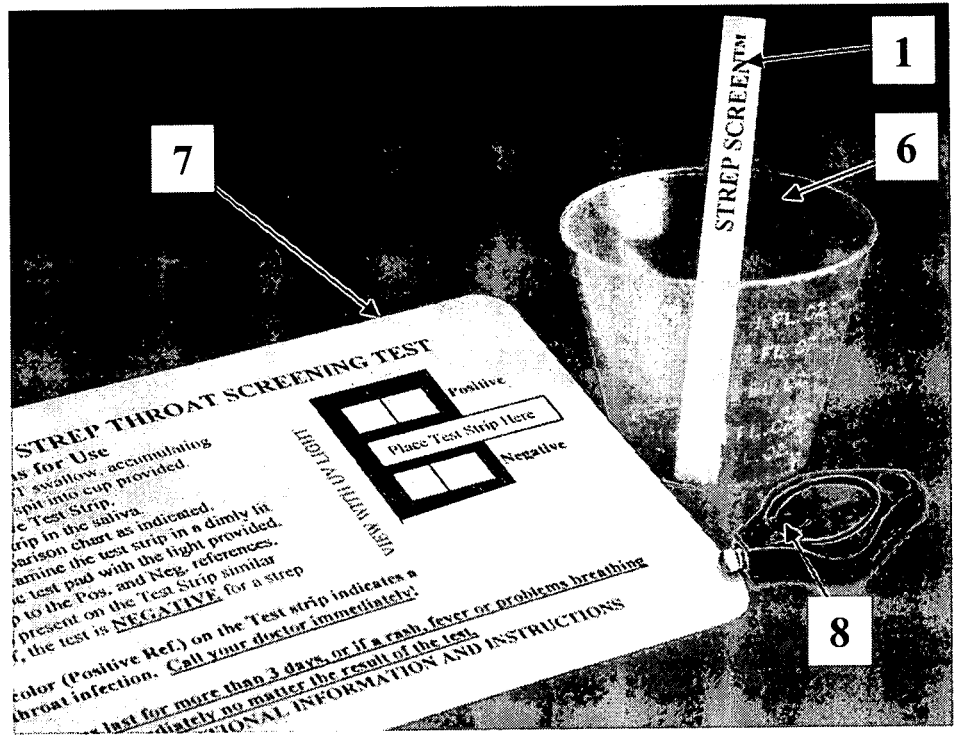
FIG. 2 is a perspective view of an inventive kit.

Referring to FIG. 2, the basic contents of a screening test kit for strep throat is shown. Test strip 1 is shown with solid matrix 3 in the bottom of a sample-receiving member in a particular form of a sample collection cup 6. Sample collection cup 6 is provided as a means to contain the biological sample in a manner so that solid matrix 3 of test strip 1 can be submerged into the sample. It should be noted that in one embodiment, at least one enzyme inhibitor is dispensed and dried in the bottom of collection cup 6 along with or instead of being in reagent 4 on solid matrix 3. This embodiment allows the inhibitor to react with and on the rogue enzymes of the biological sample prior to contacting reagent 4 on solid matrix 3 that includes the substrate.

It is appreciated that adequate time is provided for a biological fluid sample to be pretreated with an enzyme inhibitor to suppress a false positive color change of the testing results associated with a given rogue protein. This pretreatment is preferably required when a biological fluid sample, such as human saliva, is complex in nature. By way of an example, a particular enzyme targeted by an enzyme inhibitor in the present invention is trypsin.

The other kit contents shown in FIG. 2 are results reference card 7 and handheld ultraviolet light emitting diode (UV-LED) assembly 8. Results reference card 7 provides the user with a visual example of what test strip 1 looks like when the test is "negative", indicating no streptokinase is present and therefore no BHS is present in the biological sample, reference 9, and a visual example of what test strip looks like for a positive result in the presence of streptokinase and therefore indicative of BHS being present in the biological sample, reference 10. Position 11 on result reference card 7 indicates the position for test strip 1 during comparative observation of the result. UV-LED assembly 8 provides an excitation wavelength of between 300-400 nm, and preferably between 360-380 nm. The presence of the BHS exotoxin resultant active enzyme (plasmin, streptokinase-plasmin, streptokinase-plasminogen, or a combination thereof) is detected after it cleaves the fluorogenic substrate sequence providing a discernable color change as viewed unaided under UV light. When the fluorogenic substrate is cleaved by the active enzyme, the released fluorophors are excited by UV light in a specific wavelength range and the excited fluorophors emit light in a bluish fluorescent color. It is appreciated that another embodiment of the invention incorporated a chromogenic substrate into BHS reagent formula 4 would result in a color development viewed under ambient light. This typically develops a yellow color with the release of p-nitroanilide for a nitroanalide containing substrate.

When reagent formula 4 includes a fluorogenic substrate it is important and not immediately obvious that solid matrix 3 has low or no fluorescing properties. It is common in the paper industry to add UV brighteners that are excited by the ambient UV wavelengths and result in a whiter, brighter paper product. That is not desirable in this application as it represents background fluorescence, producing visible interference with the test result.

When the device is used, the patient is asked to cough a couple of times and spit into collection cup 6. If the embodiment has the rogue enzyme inhibitor desiccated in the cup, then the sample is incubated at room temperature for between 1 and 30 minutes. This allows time for the interfering enzymes to be inactivated before the sample is brought into contact with solid matrix 3 of test strip 1. Test strip 1 is removed from a protective packaging (not shown) and solid matrix 3 end is submerged in the sample for 1-2 seconds. Exposed test strip 1 is then optionally placed in a small resealable polymer bag (not shown) and sealed. This bag prevents the solid matrix with sample and reagent formula 4 from drying out changing the reaction environment, as well as containing the biologic sample for safety.

Figure 3:
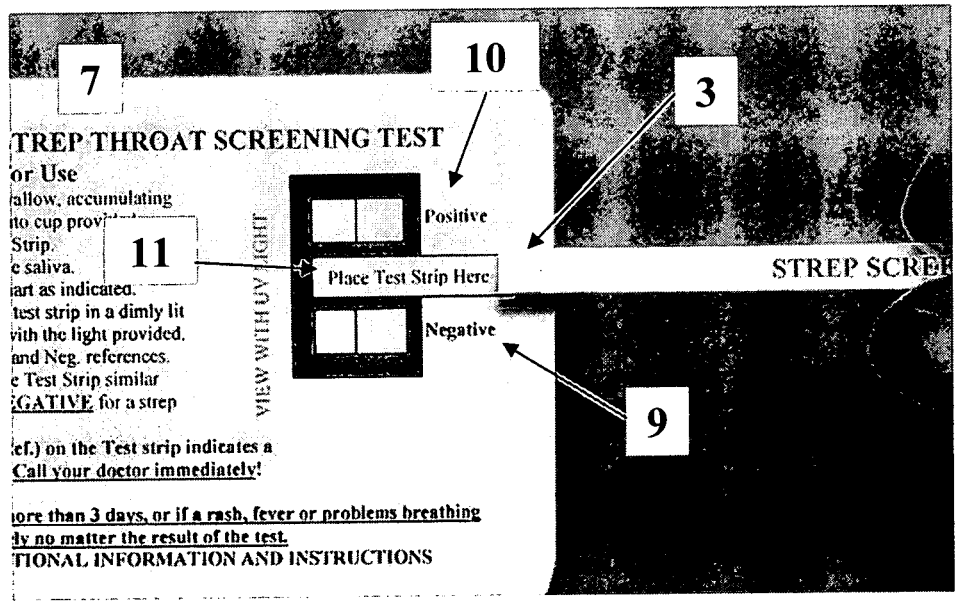
FIG. 3 is a top view of an inventive test strip and results reference card.

Test strip 1 is now placed on results reference card 7 as indicated in FIG. 3. The biochemical reaction on solid matrix 3 requires a time of approximately between 5 and 45 minutes to develop a discernable color change at room temperature. Optionally, test strip 1 in the resealable bag is exposed to temperatures greater than room temperature, but below temperatures that could denature the proteins of reagent formula 4 and of the biological sample on solid matrix 3. Since the reaction is enzymatic, the activity increases with increasing temperature to about 40° C. The temperature increase can be achieved in several ways including, but not limited to, holding solid matrix in skin contact with a user, drawing tap water into a cup that is up to about 40° C., or use of a disposable exothermic hand warmer to raise the matrix temperature up to about 40° C.

Figure 4A:
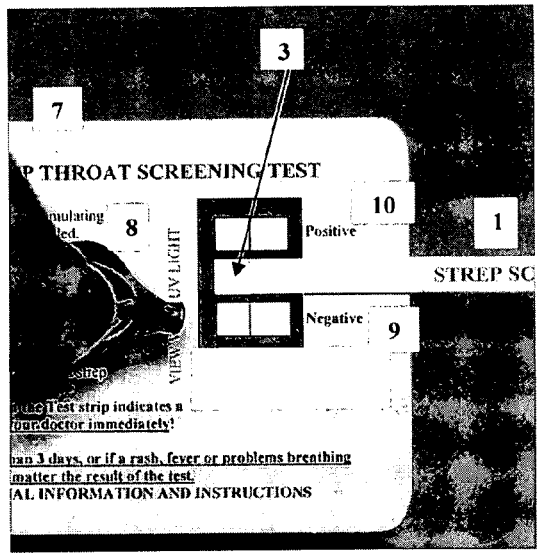
FIG. 4A shows a negative result reference for an inventive test strip under ultraviolet (UV) light.
Figure 4B:
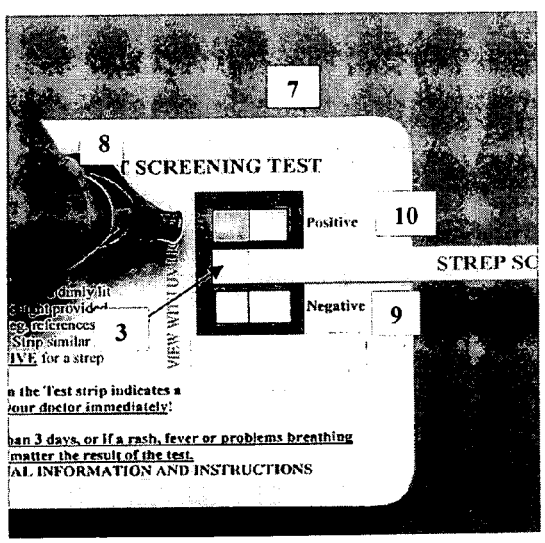
FIG. 4B shows a positive result reference under UV light.
Figure 4C:
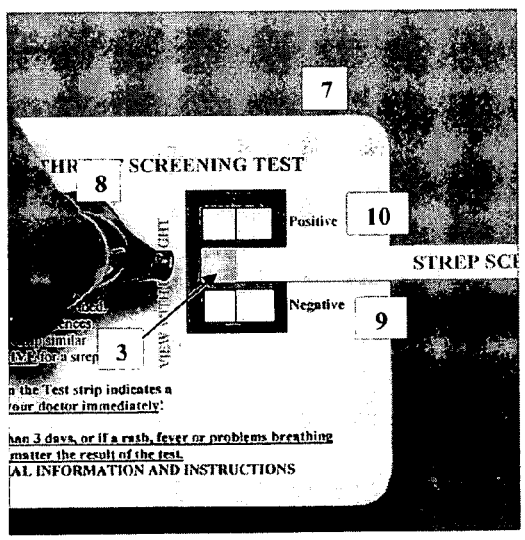
FIG. 4C shows the solid matrix of an inventive test strip under UV light.

FIGS. 4A, 4B, and 4C depict the way in which results reference card 7 is used to compare the positive and negative reference results to test strip 1 in determining if the subject from which a biological sample is obtained harbors exotoxin excreting BHS. FIG. 4A shows UV-LED 8 illuminating a negative reference result 9 that appears non-fluorescent. FIG. 4B shows UV-LED 8 illuminating a positive reference result 10 that emits a bluish fluorescence. FIG. 4C shows UV-LED 8 illuminating solid matrix 3 of test strip 1, the solid matrix 3 emits a bluish fluorescence like that of positive reference 10. This result indicates that streptokinase is present in the sample and therefore BHS is likely present in the subject as the source thereof. The result in solid matrix 3 may not exactly match the reference examples provided on card 7, but the user is instructed to decide which reference of negative 9 or positive 10 of test strip 1 is closest for determining the test result.

It is appreciated that inventive test kits for detecting BHS in biological fluids other than saliva optionally vary in host sample aliquot volumes and reagent quantity to attain desired levels of sensitivity and specificity. Factors to achieve these variations include the design of the solid matrix, type of material, and stick design, and sample collection cup design. Preferably a solid matrix collects enough biological fluid to hydrate the indicating formula. It is appreciated that excessive liquid dilutes the reagent formula and results in a less intense fluorogenic or chromogenic reaction. Modified solid matrix designs that are employed to minimize reagent dilution are polymeric film covering of the solid matrix that allows the liquid sample to wick in at least one open edge of the matrix or through the cover's porous structure. Another solid matrix design that is optionally employed is to treat the solid matrix so the molecules of reagent formula are slowed or prevented from diffusing out of the matrix.

It is appreciated that a reagent formula includes in a single volume proteinaceous substrates for streptokinase, cysteine proteinase each alone, or in combination with a cholesterol-containing membrane reactive towards streptolysin. Alternatively, the use of two or more separate reagent formulas each specific for a different BHS exotoxin affords greater selectivity to BHS since the possibility of contamination of a biological fluid sample with two or more of the exotoxins produced by BHS or a false positive becomes much less likely. It is appreciated that the multiple separate reagent formulas are readily contained on two or more solid matrix pads on test strip 1, each specific to a different BHS exotoxin. Additionally, while in a preferred embodiment streptokinase is detected through interaction with plasminogen introduced into a reagent formula, it is appreciated that a simplified streptokinase reagent formula is operative that relies on the presence of plasminogen naturally found in the biological fluid and in such an instance, the inventive reagent formula need only include a fluorogenic oligopeptide or a p-nitroanilide containing substrate that yields a color change discernable to an unaided human eye that is a substrate for the streptokinase-plasminogen complex, streptokinase-plasmin complex or plasmin. It is appreciated that an inventive reagent formula is readily made of various concentrations of fluorogenic substrate or cholesterol containing membrane containing a fluorophor to yield different formula sensitivities, color development intensities, and color development times. A starting point for the concentrations is to make a fluorogenic substrate concentration of 1 milimolar solution and in the case of streptokinase detection, a plasminogen concentration of 300 micrograms per milliliter (µg/ml). 10-20 microliters of each solution alone, or in combination with a like amount of plasminogen solution, is placed into container 1 and let dry at room temperature for streptokinase detection.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A kit for detecting an exotoxin produced by beta-hemolytic streptococcus bacterium in a biological sample of saliva collected from a subject comprising:
a sample-receiving cup or swab for collecting the saliva;
a substrate cleaved by the biological fluid collected from the subject to induce a discernable color change discernable to an unaided human eye, said substrate is selected from the group consisting of D-Val-Leu-Lys-p-Nitroanilide Dichloride, pyroGlu-Phe-Lys-p-Nitroanilide Hydrochloride, pyroGlu-Leu-Lys-p-Nitroanilide Hydrochloride, H-D-Ala-Leu-Lys-fluca 1-2Galβ1-4Glc-7-amino-4-methyl-coumarin, H-D-Val-Leu-Lys-fluca 1-2Galβ1-4Glc-7-amino-4-methyl-coumarin, N-succinyl Phe-Ala-p-Nitroanilide, Leu-p-Nitroanilide, amido-methylcoumarin, and cholesterol-containing membrane, said cholesterol-containing membrane comprising a lipid bilayer, a cholesterol, and a chromophore;
an exotoxin protein present in the biological fluid and selected from the group consisting of streptokinase, streptolysin O, streptolysin S, and streptodornase;
plasminogen;
an enzyme inhibitor inhibiting rogue protein present in the biological fluid and not preventing the exotoxin protein produced by the beta-hemolytic streptococcus bacterium from cleaving said substrate to prevent a false positive result of said color change; and
a reference card showing positive and negative control results and having instructions for the use thereof for detecting the exotoxin associated with the presence of the beta-hemolytic streptococcus in the biological sample.

2. The kit of claim 1 wherein said sample-receiving cup contains said enzyme inhibitor and said enzyme inhibitor inhibits rogue protein cleavage of said substrate to prevent a false positive result of said color change.

3. The kit of claim 1 further comprising an additional substrate digestable by a protein different than the exotoxin and selected from the group consisting of streptokinase, streptolysin O, streptolysin S, and streptodornase.

4. The kit of claim 1 further comprising an ultraviolet wavelength light emitting diode and said substrate is fluorogenic.

5. The kit of claim 1 wherein said substrate is fluorogenic or chromogenic.

6. The kit of claim 1 wherein said rogue protein is selected from the group consisting of: trypsin, kallikrein, tissue plasminogen activator (tPA), calpain, cystatin, kinases, peroxidases, dehydrogenases, phosphorylases, transferases, reductases, mutases, and/or isomerases.

7. The kit of claim 1 further comprising a protein stabilizer.

8. The kit of claim 1 further comprising a reaction enhancement additive of non-ionic detergent and a protein selected from the group consisting of fibrin, fibrinogen and a polypeptide with a lysine binding site.

9. The kit of claim 1 further comprising a cryopreservative.

10. A kit for detecting an exotoxin produced by beta-hemolytic streptococcus bacterium in a biological sample of saliva collected from a subject comprising:
a sample-receiving cup or swab for collecting the saliva;
a substrate cleaved by the exotoxin protein produced by the beta-hemolytic streptococcus bacterium present in the biological fluid collected from the subject to induce a discernable color change, the exotoxin protein selected from the group consisting of streptokinase, streptolysin O, streptolysin S, and streptodornase, said substrate is selected from the group consisting of D-Val-Leu-Lys-p-Nitroanilide Dichloride, pyroGlu-Phe-Lys-p-Nitroanilide Hydrochloride, pyroGlu-Leu-Lys-p-Nitroanilide Hydrochloride, H-D-Ala-Leu-Lys-fluca 1-2Galβ1-4Glc-7-amino-4-methyl-coumarin, H-D-Val-Leu-Lys-fluca 1-2Galβ1-4Glc-7-amino-4-methyl-coumarin, N-succinyl Phe-Ala-p-Nitroanilide, Leu-p-Nitroanilide, amido-methylcoumarin, and cholesterol-containing membrane, said cholesterol-containing membrane comprising a lipid bilayer, a cholesterol, and a chromophore;
an enzyme inhibitor inhibiting rogue protein present in the biological fluid and not correlating with the beta-hemolytic streptococcus bacterium from cleaving said substrate to prevent a false positive result of said color change discernable to an unaided human eye;
an inert solid matrix in contact with said substrate and said enzyme inhibitor; and
a reference card showing positive and negative control results and having instructions for the use thereof for detecting the exotoxin associated with the presence of the beta-hemolytic streptococcus in the biological sample.

11. The kit of claim 10 wherein said sample-receiving cup contains said enzyme inhibitor and said enzyme inhibitor inhibits rogue protein cleavage of said substrate to prevent a false positive result of said color change.

12. The kit of claim 10 further comprising an additional substrate digestable by a protein different than the exotoxin and selected from the group consisting of streptokinase, streptolysin O, streptolysin S, and streptodornase.

13. The kit of claim 10 further comprising an ultraviolet wavelength light emitting diode and wherein said substrate is fluorogenic.

14. A kit for detecting an exotoxin produced by beta-hemolytic streptococcus bacterium in a biological sample of saliva collected from a subject comprising:
   a sample-receiving cup or swab for collecting the saliva;
   a substrate cleaved by the exotoxin protein produced by the beta-hemolytic streptococcus bacterium present in the biological fluid collected from the subject to induce a discernable color change, the exotoxin protein selected from the group consisting of streptokinase, streptolysin O, streptolysin S, and streptodornase, said substrate is selected from the group consisting of D-Val-Leu-Lys-p-Nitroanilide Dichloride, pyroGlu-Phe-Lys-p-Nitroanilide Hydrochloride, pyroGlu-Leu-Lys-p-Nitroanilide Hydrochloride, H-D-Ala-Leu-Lys-fluca 1-2Galβ1-4Glc-7-amino-4-methyl-coumarin, H-D-Val-Leu-Lys-fluca 1-2Galβ1-4Glc-7-amino-4-methyl-coumarin, N-succinyl Phe-Ala-p-Nitroanilide, Leu-p-Nitroanilide, amido-methylcoumarin, and cholesterol-containing membrane, said cholesterol-containing membrane comprising a lipid bilayer, a cholesterol, and a chromophore;
   a protein stabilizer;
   an enzyme inhibitor inhibiting rogue protein present in the biological fluid and not preventing the exotoxin protein produced by the beta-hemolytic streptococcus bacterium from cleaving said substrate to prevent a false positive result of said color change discernable to an unaided human eye; and
   a reference card showing positive and negative control results and having instructions for the use thereof for detecting the exotoxin associated with the presence of the beta-hemolytic streptococcus in the biological sample.

15. The kit of claim 14 wherein said sample-receiving cup contains said enzyme inhibitor and said enzyme inhibitor inhibits rogue protein cleavage of said substrate to prevent a false positive result of said color change.

16. The kit of claim 14 further comprising an additional substrate digestable by a protein different than the exotoxin and selected from the group consisting of streptokinase, streptolysin O, streptolysin S, and streptodornase.

17. The kit of claim 14 further comprising an ultraviolet wavelength light emitting diode and said substrate is fluorogenic.

18. The kit of claim 14 wherein said rogue protein is selected from the group consisting of: trypsin, kallikrein, tissue plasminogen activator (tPA), calpain, cystatin, kinases, peroxidases, dehydrogenases, phosphorylases, transferases, reductases, mutases, and/or isomerases.

19. The kit of claim 14 further comprising plasminogen.

20. The kit of claim 14 further comprising a reaction enhancement additive of non-ionic detergent and a protein selected from the group consisting of fibrin, fibrinogen and a polypeptide with a lysine binding site.

21. The kit of claim 14 further comprising a cryopreservative.

* * * * *